United States Patent
Han et al.

(10) Patent No.: US 9,150,875 B2
(45) Date of Patent: Oct. 6, 2015

(54) OSMPT GENE FOR MODIFYING PLANT ARCHITECTURE AND INCREASING YIELD, AND USES THEREOF

(75) Inventors: Chang Deok Han, Jinju-si (KR); Yang Do Choi, Seoul (KR)

(73) Assignee: INDUSTRY-ACADEMIC COOPERATION FOUNDATION GYEONGSANG NATIONAL UNIVERSITY, Gyeongsangnam-do (KR)

( * ) Notice: Subject to any disclaimer, the term of this patent is extended or adjusted under 35 U.S.C. 154(b) by 399 days.

(21) Appl. No.: 13/520,554

(22) PCT Filed: Dec. 28, 2010

(86) PCT No.: PCT/KR2010/009447
§ 371 (c)(1),
(2), (4) Date: Jul. 3, 2012

(87) PCT Pub. No.: WO2011/090272
PCT Pub. Date: Jul. 28, 2011

(65) Prior Publication Data
US 2012/0284875 A1    Nov. 8, 2012

(30) Foreign Application Priority Data

Jan. 22, 2010 (KR) ........................ 10-2010-0005803

(51) Int. Cl.
C12N 15/29    (2006.01)
C12N 15/82    (2006.01)
C07K 14/415   (2006.01)

(52) U.S. Cl.
CPC .......... *C12N 15/8261* (2013.01); *C07K 14/415* (2013.01)

(58) Field of Classification Search
USPC .......................................... 800/290
See application file for complete search history.

(56) References Cited

U.S. PATENT DOCUMENTS

2008/0229439 A1*  9/2008  La Rosa et al. ............... 800/260

OTHER PUBLICATIONS

Liu et al. (A collection of 10,096 indica rice full-length cDNAs reveals highly expressed sequence divergence between Oryza sativa indica and japonica subspecies, 65 Plant Mol Biol, 403-415 (2007)).*
International Search Report for PCT/KR2010/009447.
NCBI GenBank Accession No. ABF94851, Jul. 7, 2006.
Wang et al. OsLIC, a Novel CCCH-Type Zinc Finger Protein with Transcription Activation, Mediates Rice Architecture via Brassinosteroids Signaling. PLoS One. Epub Oct. 27, 2008, vol. 3, No. 10, pp. e3521.

* cited by examiner

*Primary Examiner* — Ashwin Mehta
*Assistant Examiner* — Stephen Uyeno
(74) *Attorney, Agent, or Firm* — The PL Law Group, PLLC

(57) ABSTRACT

The present invention relates to a rice (*Oryza sativa*)-induced *Oryza sativa* modifier of plant type (OsMPT) protein which is involved in adjusting tillering angle or angle of attachment between a leaf and a stem, a gene encoding the protein, a recombinant plant expression vector including the gene, a plant transformed by the recombinant plant expression vector, a method for modifying architectures of plants by adjusting the level of the gene in the cells thereof, to a method for manufacturing an architecturally modified plant transformed by the gene, to a plant with increased yield which is manufactured by the method, and to a composition containing the gene for modifying the architectures of plants and increasing the yield thereof.

9 Claims, 9 Drawing Sheets

Dongjin*    MPT OX
* Dongjin: An elite Japonica rice variety

US 9,150,875 B2

OSMPT GENE FOR MODIFYING PLANT ARCHITECTURE AND INCREASING YIELD, AND USES THEREOF

CROSS REFERENCE TO RELATED APPLICATIONS AND CLAIM OF PRIORITY

This patent application is a National Phase application under 35 U.S.C. §371 of International Application No. PCT/KR2010/009447, filed Dec. 28, 2010, which claims priority to Korean Patent Application number 10-2010-0005803, filed Jan. 22, 2010, entire contents of which are incorporated herein by reference.

BACKGROUND

1. Technical Field

The present invention relates to an OsMPT gene derived from rice (Oryza sativa) for modifying plant architecture and increasing yield, and uses thereof. More specifically, the present invention relates to a recombinant plant expression vector including the OsMPT gene, a plant transformed with the recombinant plant expression vector, a process for modifying plant architecture and increasing yield by controlling the cellular level of the gene, a process for producing a plant with modified architecture and a plant with increased yield by transforming a plant with the gene, and a composition including the gene for modifying plant architecture and increasing yield.

2. Background Art

Rice (Oryza sativa) is the most important food crop and a primary food source for more than a third of the world population. With the swift growth of rice consumers, higher rice production is required more than ever. Thus, the rice varieties with higher yield potential and yield stability are needed to meet the challenges of increased rice production [Khush 1997, Plant Mol. Biol. 35, 25-34]. The structure of the aerial part of a plant, referred to as plant architecture, has a great influence on production. In fact, tiller angle is an important characteristic for determining plant architecture in rice, i.e., wider tiller angle would increase leaf shade, whereas a narrower tiller angle is favored for dense planting. As such, erect growth (a narrow tiller angle), which allows relatively effective high-yield cultivation, has been targeted and continuously selected by plant breeders. However, to date, the molecular and genetic mechanisms controlling erect growth has remained unknown.

Although plant architecture is influenced by environmental factors, the genetic regulatory mechanisms play an important role in controlling plant architecture. There are genes known to be involved in the direct control of rice tiller angle; PROG1 (PROSTRATE GROWTH 1) encodes a single $C_2H_2$ zinc finger protein and prog1 mutants exhibited erect growth, greater grain number and higher grain yield in rice [Tan, et. al., 2008, Nat. Genet. 40, 1360-1364]. Mutation of TAC1 (Tiller Angle Control 1) caused rice plants to show extremely erect tillers and to be able to adapt highly dense cultivation in the field [Yu, et. al., 2007, Plant J. 52, 891-898]. LAZY1, TAC1 and PROG1 are strongly expressed in the leaf sheath pulvinus, tiller base, or laminar joint between leaf blade and leaf sheath.

SUMMARY

The present invention is devised in view of the above-described needs. Specifically, inventors of the present invention determined the function of OsMPT gene by analyzing not only mutants but also overexpressing plants and provided a method for modifying plant architecture and increasing yield by using the gene.

In order to solve the problems described above, the present invention provides OsMPT (Oryza sativa Modifier of Plant Type) protein originating from rice (Oryza sativa).

Further, the present invention provides a gene which encodes the OsMPT gene.

Further, the present invention provides a recombinant plant expression vector which includes the OsMPT gene.

Further, the present invention provides a plant transformed with the recombinant plant expression vector.

Further, the present invention provides a method for modifying plant architecture by controlling cellular level of the OsMPT polypeptide.

Further, the present invention provides a method for producing a plant with modified architecture by transforming a plant with the OsMPT gene.

Further, the present invention provides a composition including the OsMPT gene for modifying plant architecture.

Further, the present invention provides a method for producing a plant with increased yield by transforming a plant with the OsMPT gene.

Further, the present invention provides a plant with increased yield that is produced by the method of the invention.

Still further, the present invention provides a composition including the OsMPT gene for increasing yield of a plant.

According to the present invention, a method for controlling the cellular level of OsMPT protein or a method for modifying plant architecture by transforming a plant with the OsMPT gene is provided. With the methods, a transformed plant with modified tiller angle or different angle between a stem and leaf attachment can be produced. In particular, such a transformed plant can produce high yield.

DETAILED DESCRIPTION

Figure 1:
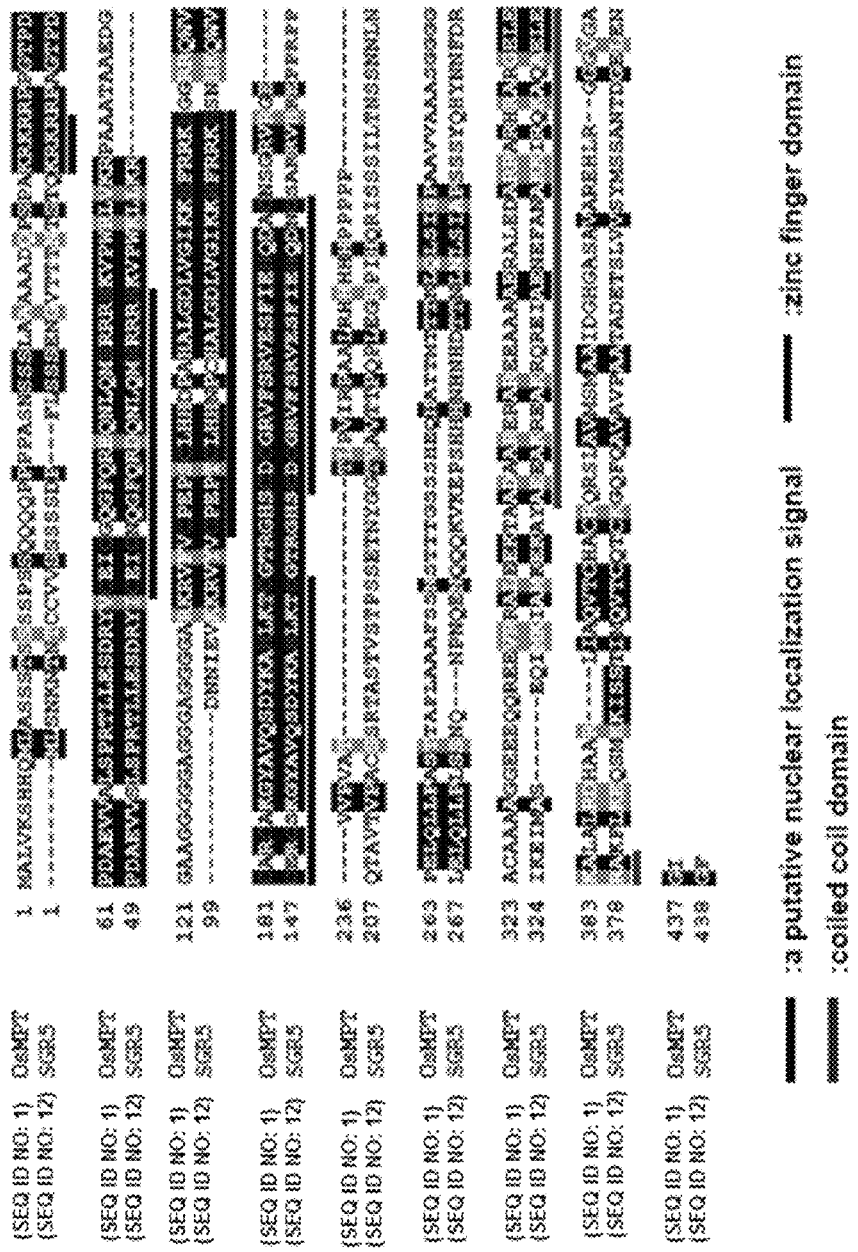
FIG. 1 illustrates an alignment of amino acid sequences of OsMPT (SEQ ID NO: 1) and Arabidopsis SGR5 (SEQ ID NO: 12). Identical amino acids are in black boxes while similar ones are in gray boxes. A putative nuclear localization signal sequence, zinc finger domain, and coiled coil domain are underlined. The coiled coil domain is from the 344th locus to the 379th locus of SGR5 in FIG. 1, and the other underlined sequence is for zinc finger domain. OsMPT shares 42% identity and 54% similarity with SGR5 at the amino acid level. Excluding the 22 amino acids between the first and second zinc fingers, the two genes share 84% identity.

In order to achieve the purpose of the invention as described above, the present invention provides OsMPT (*Oryza sativa* Modifier of Plant Type) protein originating from rice (*Oryza sativa*), in which the OsMPT protein has an amino acid sequence of SEQ ID NO: 1.

The scope of the OsMPT protein of the present invention includes a protein having an amino acid sequence represented by SEQ ID NO: 1 that is isolated from rice (*Oryza sativa*), and functional equivalents of said proteins. The term "functional equivalents" means that, as a result of addition, substitution or deletion of amino acid residues, it has an amino acid sequence with at least 70%, for example, at least 80%, for another example, at least 90%, and for still another example, at least 95% identity with the amino acid sequence that is represented by SEQ ID NO: 1, thus indicating a protein which has substantially the same physiological activity as the protein represented by SEQ ID NO: 1.

Further, the present invention provides a gene which encodes the OsMPT protein. The gene of the present invention includes both genomic DNA and cDNA which encode the OsMPT protein. Preferably, the gene of the present invention may include the cDNA represented by SEQ ID NO: 2 and genomic DNA represented by SEQ ID NO: 3. Further, variants of said nucleotide sequence are also within the scope of the present invention. Specifically, said gene may include a nucleotide sequence with at least 70%, for example, at least 80%, for another example at least 90%, and for still another example, at least 95% identity with the nucleotide sequences of SEQ ID NO: 2 or SEQ ID NO: 3. The "sequence identity %" for a certain polynucleotide is determined by comparing two nucleotide sequences that are optimally arranged with a region to be compared. In this regard, a part of the polynucleotide sequence in a region to be compared may include an addition or a deletion (i.e., a gap) compared to a reference sequence (without any addition or deletion) relative to the optimized arrangement of the two sequences.

The OsMPT gene of the invention is expressed in a pulvinus-specific manner.

The present invention also provides a recombinant plant expression vector including the OsMPT gene according to the present invention. According to the recombinant plant expression vector of the invention, the OsMPT gene may have a nucleotide sequence of SEQ ID NO: 2.

The term "recombinant" indicates a cell which replicates a heterogeneous nucleotide or expresses said nucleotide, a peptide, a heterogeneous peptide, or a protein encoded by a heterogeneous nucleotide. Recombinant cell can express a gene or a gene fragment in a form of a sense or antisense, that are not found in natural state of cell. In addition, a recombinant cell can express a gene that is found in the natural state, provided that said gene is modified and re-introduced into the cell by an artificial means.

The term "vector" is used herein to refer DNA fragment (s) and nucleotide molecules that are delivered to a cell. Vector can replicate DNA and be independently reproduced in a host cell. The terms "delivery system" and "vector" are often interchangeably used. The term "expression vector" means a recombinant DNA molecule including a desired coding sequence and other appropriate nucleotide sequences that are essential for the expression of the operably linked coding sequence in a specific host organism. A promoter, an enhancer, a stop signal, and a polyadenylation signal that can be used for eukaryotic cells are well known in the field.

A preferred example of the recombinant vector is Ti-plasmid vector which can transfer a part of itself, i.e., so-called T-region, to a plant cell when the vector is present in an appropriate host such as *Agrobacterium tumefaciens*. Other types of Ti-plasmid vector (see, EP 0 116 718 B1) are currently used for transferring a hybrid gene to protoplasts that can produce a new plant by appropriately inserting a plant cell or hybrid DNA to a plant genome. Especially preferred form of Ti-plasmid vector is a so-called binary vector which has been disclosed in EP 0 120 516 B1 and U.S. Pat. No. 4,940,838. The binary vector that is preferably used for the present invention may be pGA1611, but not limited thereto. Other appropriate vectors that can be used for introducing the DNA of the present invention to a host plant can be selected from a double-stranded plant virus (e.g., CaMV), a single-stranded plant virus, and a viral vector which can be originated from Gemini virus, etc., for example a non-complete plant viral vector. Use of said vector can be especially advantageous when a plant host cannot be appropriately transformed.

Expression vector preferably includes at least one selection marker. Said selection marker is a nucleotide sequence having a property which allows a selection based on a common chemical method. Any kind of gene that can be used for the differentiation of transformed cells from non-transformed cells can be a selection marker. Example includes, a gene resistant to herbicide such as glyphosate and phosphinotricin, and a gene resistant to antibiotics such as kanamycin, G418, bleomycin, hygromycin, and chloramphenicol, but not limited thereto.

According to the recombinant vector of the present invention, the promoter can be CaMV 35S promoter, actin promoter, ubiquitin promoter, pEMU promoter, MAS promoter, or histone promoter, but not limited thereto. The term "promoter" indicates a region of DNA located upstream of a structure gene, and it corresponds to a DNA molecule to which an RNA polymerase binds to initiate transcription. The term "plant promoter" indicates the promoter that can initiate transcription in a plant cell. The term "constitutive promoter" indicates the promoter that is active under most environmental conditions and cell growth or differentiation state. Since selection of a transformant can be made for various tissues at various stages, the constitutive promoter may be preferred for the present invention. Thus, selection property is not limited by a constitutive promoter. More preferably, it may be a ubiquitin promoter, but not limited thereto.

In the above-described recombinant vector of the invention, any kind of a typical terminator can be used. Example includes, nopalin synthase (NOS), rice α-amylase RAmy1 A terminator, phaseoline terminator, and a terminator for Octopine gene of *Agrobacterium tumefaciens*, etc., but are not limited thereto. Regarding the necessity of terminator, it is generally known that such region can increase a reliability and an efficiency of transcription in plant cells. Therefore, the use of terminator is highly preferable in view of the context of the present invention.

The present invention also provides a plant that is transformed with the plant expression recombinant vector of the invention. Any kind of a host cell known in the pertinent art can be used if stable and continuous cloning and expression of the vector of the present invention can be achieved in eukaryotic cells by using it. Examples include strains belonging to the genus *Bascillus* such as *E. coli* JM109, *E. coli* BL21, *E. coli* RR1, *E. coli* LE392, *E. coli* B, *E. coli* X 1776, *E. coli* W3110, *Bascillus subtilus, Bascillus thuringiensis*, and the like, *Salmonella typhimurium*, intestinal flora and strains such as *Serratia marcescens* and various *Pseudomonas* Spp. and the like. In addition, when the vector of the present invention is transformed in an eukaryotic cell, a host cell such as *Saccharomyce cerevisiae*, an insect cell, a human cell (e.g., CHO cell line (Chinese hamster ovary), W138, BHK, COS-7,293, HepG2, 3T3, RIN and MDCK cell line), a plant cell line and the like can be used. Preferably, the host cell is a plant cell. More preferably, it is rice (*Oryza saliva*). Most preferably, it is Dongjin rice cultivar, but not limited thereto.

When a host cell is a prokaryotic cell, transfer of the vector of the present invention into a host cell can be carried out according to a $CaCl_2$ method, Hanahan's method, and an electroporation method, etc. In addition, when a host cell is an eukaryotic cell, the vector of the present invention can be transferred into a host cell according to a microscopic injection method; a calcium phosphate precipitation method, an electroporation method, a liposome-mediated transformation, a DEAE-dextran treatment method and a gene bombardment method, etc.

Also provided by the present invention is a method for modifying plant architecture by controlling cellular level of OsMPT polypeptide.

The OsMPT polypeptide of the invention is specifically expressed in pulvinus tissue of a plant and it is involved in control of tiller angle or an angle between a stem and leaf attachment. These functions of the OsMPT are first identified by the inventors of the present invention. The OsMPT is preferably a polypeptide including an amino acid sequence of SEQ ID NO: 1. Meanwhile, the polypeptide may be a functional equivalent of an amino acid sequence of SEQ ID NO: 1. The term "functional equivalent" as used herein has the same definition as described above and it means a polypeptide which has substantially the same activity as the OsMPT. As used herein, the term "substantially the same activity" means the involvement in determination of plant architecture. The functional equivalent includes an amino acid variant in which part of the amino acid sequence represented by SEQ ID NO: 1 is substituted, deleted, or added. Amino acid substitution is preferably a conservative substitution. Examples of the naturally-occurring conservative substitution of an amino acid include the followings: aliphatic amino acids (Gly, Ala, Pro), hydrophobic amino acids (Ile; Leu, Val), aromatic amino acids (Phe, Tyr, Trp), acidic amino acids (Asp, Glu), basic amino acids (His, Lys, Arg, Gln, Asn), and sulfur-containing amino acids (Cys, Met). Deletion of an amino acid is preferably located in a region which is not directly involved in the activity of OsMPT of the invention.

Further, included within the scope of the functional equivalents is a polypeptide derivative with partially modified chemical structure of the polypeptide while the main skeleton and physiological activity of the OsMPT are maintained. Examples thereof include a fusion protein or the like which is obtained by fusion with other protein for structural modification including modification of stability, storing property, volatility, solubility or the like of the polypeptide of the invention while physiological activity of the peptide is maintained.

As used herein, the term "plant architecture" means an external structure or shape of a plant or each shape of a tissue or an organ like a leaf, a stem, a root, and a flower, and overall shape resulting from combination of individual shapes. For example, it indicates a tiller angle, an angle of a laminar joint, or an angle between a stem and leaf attachment, but not limited thereto.

According to the present invention, growth direction of part or whole tissue or organ of a plant vary depending on cellular level of the polypeptide represented by SEQ ID NO: 1 or functional equivalent thereof. Thus, in the present invention, any change in plant architecture mainly indicates a change in angles of leaves and tillers of the plant.

The cellular level indicates an amount present within a cell, and it may be controlled by various methods that are known to a person skilled in the art. The cellular level may be controlled at the level of transcription or post-transcription, although it is not specifically limited thereto. Control of the transcription level may be performed by following any method for enhancing gene expression that is well known to a person skilled in the art, i.e., a method of enhancing gene expression via production of a recombinant expression vector including a promoter linked to a gene which encodes SEQ ID NO: 1 or a functional equivalent thereof or a method of inserting an expression regulating sequence for enhancing gene expression near the gene which encodes SEQ ID NO: 1 or a functional equivalent thereof, or any method for suppressing gene expression, i.e., a method of suppressing the activity of a promoter or the function of a protein by introducing a mutation to a promoter or gene, a method of expressing an anti-sense gene, or a method based on RNAi or micro RNA.

Control of post-transcription level may be performed by a method of enhancing or suppressing protein expression that is well known to a person skilled in the art, for example, a method of enhancing or suppressing stability of mRNA which is transcribed from the gene which encodes SEQ ID NO: 1 or a functional equivalent thereof as a template, a method of enhancing or suppressing stability of the protein or polypeptide, or a method of enhancing or suppressing activity of the protein or polypeptide.

Specific examples of the method include co-suppression which is achieved by transformation with a DNA sequence encoding RNA like group 1 intron type, M1RNA type, hammerhead type, hairpin type, or micro RNA type which reacts with a transcribed mRNA or by transformation of DNA having a sequence either the same or similar to a target gene sequence.

Preferably, controlling the cellular level of the polypeptide represented by SEQ ID NO: 1 or an equivalent thereof can be performed by a method of increasing or decreasing expression of polynucleotide encoding the polypeptide. Preferably, it is achieved by increasing the expression of the polynucleotide. As for a method for increasing or decreasing the expression, a method well known to a person skilled in the art may be employed. For example, the expression can be increased by producing a recombinant expression vector including a polynucleotide encoding the polypeptide represented by SEQ ID NO: 1 or an equivalent thereof linked to a promoter, or it can be decreased by producing a recombinant expression vector including an anti-sense polynucleotide against the polynucleotide linked to a promoter. Preferably, the polynucleotide may have a base sequence represented by SEQ ID NO: 2.

Examples of the plant include, although not specifically limited, angiosperms like rice, wheat, barley, oat, rye, lawn grass, bamboo shoot, corn, sugar cane, millet, taro, asparagus, onion, garlic, scallion, leek, wild rocambole, hemp, ginger, bean, and canola. It is preferably rice, and more preferably Dongjin rice cultivar. The plant tissue affected by a change in OsMPT protein expression may be one determining leaf and tiller angles.

Also provided by the present invention is a method for producing a plant with modified architecture including a step of transforming a plant with a polynucleotide which encodes OsMPT or a functional equivalent thereof and a plant with modified architecture prepared by the method. The polynucleotide may preferably have a base sequence represented by SEQ ID NO: 2. Transformation of a plant may be carried out according to a transformation technique that is well known to a person skilled in the art. Preferred examples of the method that can be used include transformation using *Agrobacterium*, microprojectile bombardment, electroporation, PEG-mediated fusion, microinjection, liposome-mediated method, in-planta transformation, vacuum infiltration method, floral meristem dipping method, and *Agrobacteria* spraying method. More preferably, transformation using *Agrobacterium* can be used. Still more preferably, transformation using "LBA4404', which is an *Agrobacterium* cell line, can be used, but not limited thereto.

In such case, the polynucleotide may be in a state in which it is operably linked to a promoter so that it can be expressed in a transformed plant, e.g., a recombinant plant expression vector in which the polynucleotide is operably linked to a promoter. The term "operably linked" means that one nucleic acid fragment is bonded to other nucleic acid fragment so that its function or expression is affected by other nucleic acid fragment. The promoter and recombinant expression vector are as defined above.

The transformed plant cell may be any one of liquid culture, callus, or protoplast culture, and it may be converted into a plant tissue or organ after differentiation. Plant cell culture includes isolating part of a plant from a mother plant and culturing aseptically under an appropriate condition to grow the plant, and it may be carried out by any method well known to a person skilled in the art like liquid culture of a tissue fragment, callus culture of a tissue fragment, and protoplast culture. Conditions and method for culture can be adopted from those well known to a person skill in the art. Differentiation of the cultured plant cells into a plant includes inducing differentiation of callus and cultured plant cells in protoplast state under an appropriate condition and differentiating them into a plant tissue or plant, and conditions and method for differentiation can be adopted from those well known to a person skill in the art.

Examples of the plant include, although not specifically limited, angiosperms like rice, wheat, barley, oat, rye, lawn grass, bamboo shoot, corn, sugar cane, millet, taro, asparagus, onion, garlic, scallion, leek, wild rocambole, hemp, ginger, bean, and canola. It is preferably rice, and more preferably Dongjin rice cultivar.

Also provided by the present invention is a composition including the OsMPT gene for modifying plant architecture, in which the OsMPT gene specifically expressed in pulvinus of a plant is involved in control of a tiller angle, an angle of a laminar joint, or an angle between a stem and leaf attachment. According to the composition of the present invention, the OsMPT gene preferably has a base sequence of SEQ ID NO: 2 or SEQ ID NO: 3. According to the composition of the present invention, the OsMPT gene may include an insertion, a substitution, or a deletion of a specific base sequence of the OsMPT gene.

Also provided by the present invention is a method for producing a plant with increased yield by transforming a plant with the OsMPT gene.

As used herein, the term "yield" indicates a measurable production amount of a plant with economic value. Typically, it is related to a certain crop, area, and period. Each plant part directly contributes to the yield based on number, size, an/or weight, or actual yield is a yield per crop acre and year and it is determined by dividing the total production amount (including harvested and evaluated production amount) by the cultivation acres. The "yield" of a plant may be related with a biomass of a vegetative tissue (i.e., biomass of roots and/or young stems), a reproductive organ, and a propagule (e.g., seeds) of a plant.

In case of rice, for example, increased yield is exhibited by any one of the followings: increased number of plant per hectare or acre; increased number of ears (fruits) per plant; increased panicle number, increased number of grains per panicle, increased grain weight, increased weight of thousand grains, increased length/diameter of a fruit, and; increased seed formation ratio (number of filled seeds/number of total seeds×100).

As used herein, the terms "increase", "enhance", and "strengthen" can be used interchangeably, and they indicates at least 3%, for example, 4%, 5%, 6%, 7%, 8%, 9%, or 10%, for another example, at least 15% or 20%, and for still another example, at least 25%, 30%, 35%, or 40% increase in yield and/or growth of a plant compared to a control group plant as defined in the present invention.

Also provided by the invention is a plant with increased yield that is produced by the method of the invention.

Examples of the plant include, although not specifically limited, angiosperms like rice, wheat, barley, oat, rye, lawn grass, bamboo shoot, corn, sugar cane, millet, taro, asparagus, onion, garlic, scallion, leek, wild rocambole, hemp, ginger, bean, and canola. It is preferably rice, and more preferably Dongjin rice cultivar.

Also provided by the invention is a composition including the OsMPT gene for increasing yield of a plant. According to the composition of the present invention, the OsMPT gene preferably has a base sequence of SEQ ID NO: 2 or SEQ ID NO: 3. According to the composition of the present invention, the OsMPT gene may include an insertion, a substitution, or a deletion of a specific base sequence of the OsMPT gene.

The present invention will now be described in greater detail with reference to the following examples. However, it is only to specifically exemplify the present invention and in no case the scope of the present invention is limited by these examples.

MATERIALS AND METHODS

1. Plant Material and Growth Condition

The 'Dongjin' japonica cultivar (i.e., Dongjin rice) were used as the wild type control. Ds transposon mutant pool was used to isolate OsMPT mutants. Among the BR variants used in the invention, d61-1 mutant has been kindly provided by Professor Matsuoka at Nagoya University in Japan while d11-1 and d2-2 mutants have been kindly provided by Professor Hee-Jong Go at Seoul National University in South Korea. Plants were grown in the paddy field from June to October in South Korea. Plants were also grown in a growth chamber. The conditions include 26° C. and 16 hours light/8 hours dark.

2. Isolation of Mutant and Revertant

Figure 2:
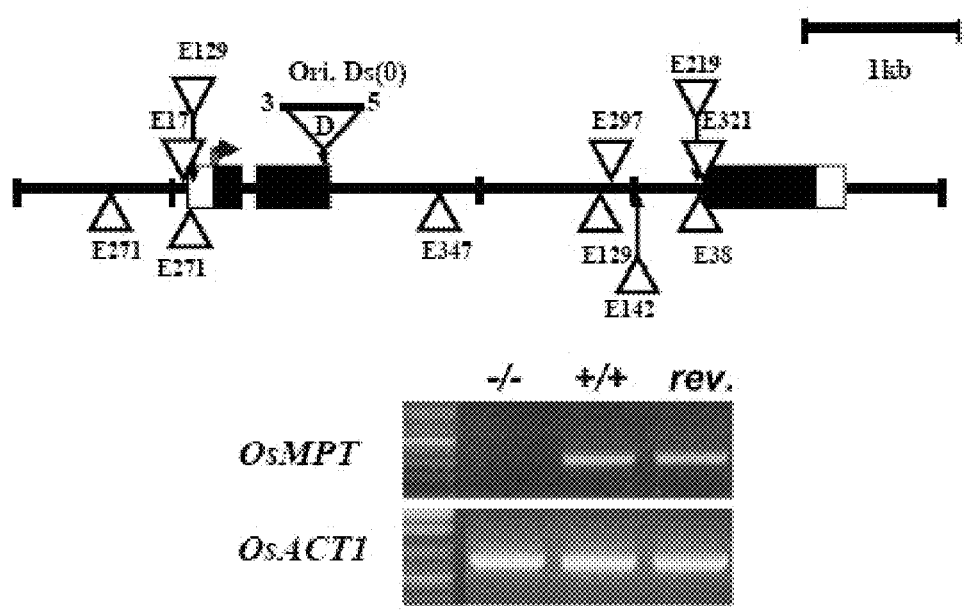
FIG. 2 illustrates genomic structures of Ds inserted alleles and expression of OsMPT::Ds and its revertant. The revertant allele was obtained by remobilizing Ds at the original site (Ori. Ds). The original insertion mutant and its revertant were examined for OsMPT expression.

OsMPT was identified via sequencing insertions of Ds transposant populations. Sequencing of the flanking regions of the Ds insertion site indicated that the transposon was inserted into the third $C_2H_2$ zinc finger motif in the second exon of OsMPT (FIG. 2). RT-PCR using gene-specific primers showed that transcripts are not expressed in the mutant line (FIG. 2). To obtain other mutant alleles and revertant alleles, OsMPT (OsMPT:Ds) generations containing Ac were used for regeneration process via tissue culture. Eleven new transposed Ds insertion mutants in the OsMPT gene locus and revertants were isolated from regenerated plants (FIG. 2).

3. Cloning of OsMPT cDNA

Full length OsMPT cDNA was isolated by RACE-PCR and RT-PCR. 5' and 3' ends including UTR (non-translated region) were cloned by RACE-PCR and the other was amplified by RT-PCR. Primer pairs used were: 5'-acctgtccgactccag-cagcgtcctcg-3' (SEQ ID NO: 4) for 5' RACE-PCR; 5'-gta-caacttgtacgttc-acgtgtgta-3' (SEQ ID NO: 5) for 3' RACE-PCR; 5'-cggcatcaagaagcacttc-3' (SEQ ID NO: 6) and 5'-ggatgatggtgatgatgccgca-3' (SEQ ID NO: 7) for RT-PCR. cDNA was synthesized using BD SMART™ RACE cDNA Amplification Kit (Clontech, USA) by RACE-PCR. cDNA was prepared from RNA of a tissue around SAM by RT-PCR using Superscript II reverse transcriptase (Invitrogen, USA).

4. Production of Overexpressing Transgenic Plants

For generating OsMPT overexpressing transgenic plants, constitutive Ubiquilin promoter was fused with OsMPT full length cDNA by cloning into a binary vector pGA1611. The construct was transformed into *Agrobacterium* strain 'LBA4404' and then introduced into callus of Dongjin rice cultivar, and as a result, transgenic plants were produced.

5. RNA Quantification

Total cellular RNA was isolated by using the TRIZOL reagent (Molecular Research Center, Inc.) or RNeasy Plant Mini Kits (Qiagen). For quantitative RT-PCR, first-strand cDNA was synthesized using the Moloney murine leukemia virus (MMLV) reverse transcriptase RNaseH (Toyobo) in a 25 µl reaction mixture containing DNase-treated RNA and an oligo dT 12-18 primer (Invitrogen), according to the manufacturer's instructions. The reaction mixture (1 µl aliquot) was then used for PCR amplification. ACT1 mRNA (actin1) was used for normalization in quantifying cDNA. Primer pairs used were: 5'-CGAGGCGCAGTCCAAGAG-3' (SEQ ID NO: 8) and 5'-CCCAGTTGCTGACGATACCA-3' (SEQ ID NO: 9) for ACT1 [McElroy et. al., 1990, *Plant Mol. Biol.* 14: 163-171]; 5'-CGGCATCAAGAAGCACTTC-3' (SEQ ID NO: 10) and 5'-ggatgatggtgatgatgccgca-3' (SEQ ID NO: 11) for OsMPT. The reactions consisted of an initial denaturation for 5 min at 95° C., followed by 94° C. for 15 sec, 60° C. for 30 sec, and 72° C. for 40 sec. The number of cycles used for each amplification were: ACT1, 25 cycles; OsMPT, 32 or 35 cycles. Amplified PCR products were separated on a 1.5% agarose gel.

6. Evaluation of Phenotype and Yield 6-1. Evaluation Setup

Field performance of the OsMPT overexpressors were examined. Specifically, two transgenic lines (i.e., OX14 and OX19) were selected and propagated. For the field test, two lines of each of the two independent transgenic plant (OX14 and OX19) were planted along with their non-transgenic wild type siblings (i.e., WT(OX14) and WT(OX19)). Plants either with or without T-DNA were separately bred in the first segregating generation after the transformation. The lines with T-DNA were designated as OX14 and OX19, respectively, and the lines without T-DNA were designated as WT(OX14) and WT(OX19), respectively. Total six lines were tested in two different planting densities (30×15 cm (23.3 plants/m$^2$) and 15×15 cm (46.7 plants/m$^2$). Those lines were OX14-1, OX14-2, WT(OX14), OX19-1, OX19-2, and WT(OX19). Plants were grown in the GMO field of the experiment station of Rural Development Administration (RDA) at Milyang, South Korea. Cultivation and management practices were performed using standard rice cultivation methods recommended by RDA of South Korea. Each test plot was of a size of 2×1.5 m and was replicated twice in randomized blocks. In each test plot, total 70 and 140 plants were transplanted for standard density and high density, respectively. Three neighboring individual plants were harvested from each plot, excluding marginal plants. Non-transgenic control line of OX19 (WT (OX19)), which has been cultivated at standard planting distance, was lost due to lodging, and therefore excluded.

6-2. Observation of Growth and Phenotype of OsMPT Overexpressor Line in Paddy Field In order to determine the growth and phenotype of OsMPT overexpressor line in a colony of outdoor paddy field, the plants were cultivated at two planting densities, i.e., standard transplantation distance of 30×15 cm and the dense planting distance of 15×15 cm in a GMO field, and the observation was made thereafter.

6-3. Parameter Measurement

Around 30 plants and 60 plants in neighboring rows were harvested from the standard density field and high density field, respectively. However, the non-transgenic control line of OX19 (WT (OX19)), which has been cultivated at standard planting distance, was lost in both fields due to lodging. The following harvest indices were measured; culm length, panicle length, number of panicles per plant, total number of spikelets, total number of filled seeds, and total grain weight.

Example 1

OsMPT Encodes a Protein Containing Zinc Finger Motif

OsMPT encodes a nuclear protein with four zinc finger motifs ($C_2H_2C_2H_2C_2HC$ $C_2HC$). These motifs are similar to the zinc finger motif found in the corn flowering gene "Id1 (Indeterminate 1)", which has been published before (Colasanti, et. al., 2006, *BMC Genomics* 7, 158).

Example 2

OsMPT is a Functional Orthologue to Gravity Response-Related SCR5 of *Arabidopsis*

SGR5 (Shoot Gravity Response 5) of *Arabidopsis* has been reported to be involved in gravity response (Morita et al., 2006, *Plant J.* 47, 619-628). OsMPT shares 42% identity and 54% similarity with SGR5 at the amino acid level (FIG. 1). Currently, a manuscript on the gravity response of OsMPT is being prepared to report the following data; OsMPT is specifically expressed in metaxylem, pulvinal tissues (i.e., gravity sensing organ found in Gramineae), and laminar joints (i.e., joints between leaf blade and leaf sheath). Mutants showed severe reduction in gravitropism. Overexpressors of OsMPT showed an enhanced gravitropic response.

Example 3

Figure 3:
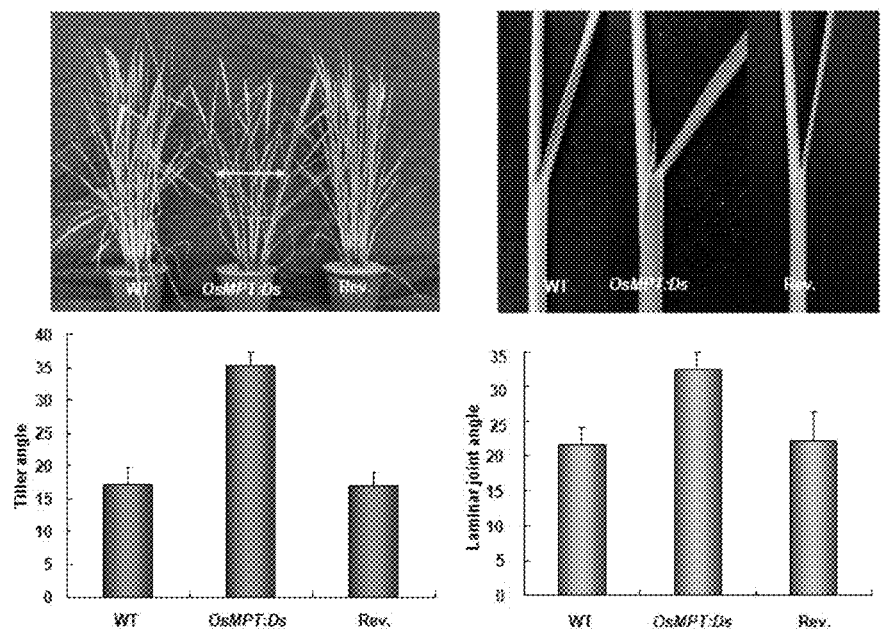
FIG. 3 illustrates tiller and laminar joint (i.e., joint between leaf blade and leaf sheath) angles of non-transgenic control line (WT; left), OsMPT::DS (middle), and revertant (Rev: right). Tiller angles are measured from a main culm to the outermost tiller. Laminar joint angles were measured from stem to the lowest part of leaf blade.
Figure 4:
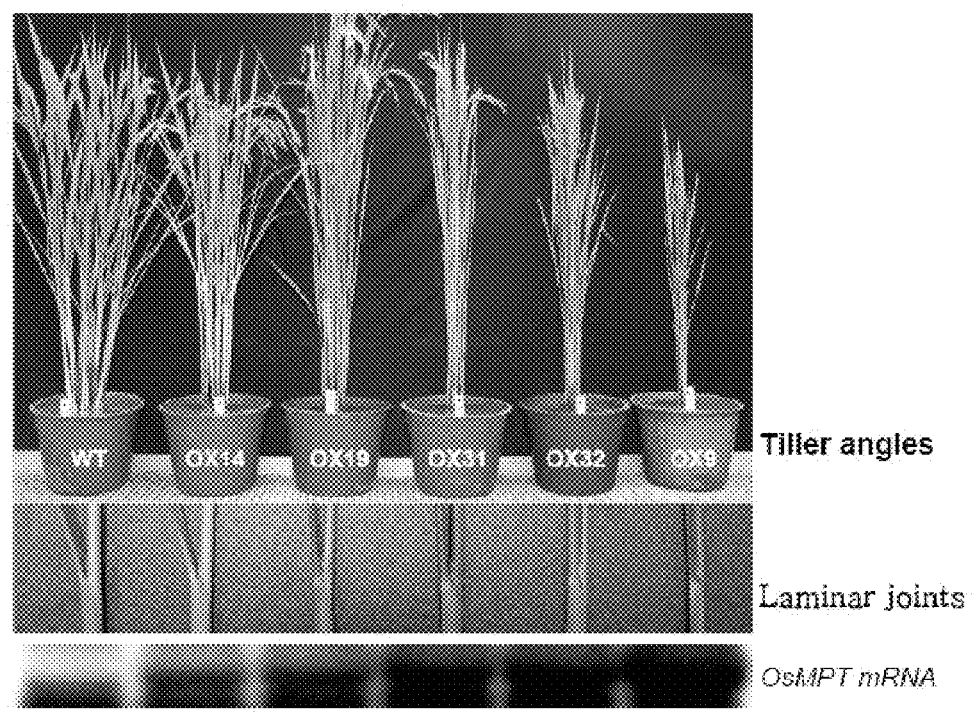
FIG. 4 illustrates erect plant type of OsMPT overexpressors (OX). The overexpressors produce erect type plants by decreasing angles of tiller and laminar joint. The extent of these angles is dependent upon the level of OsMPT mRNA. Northern blot analysis given at the bottom part of the figure shows the expression level of each OsMPT overexpressor (OX) line.
Figure 5:
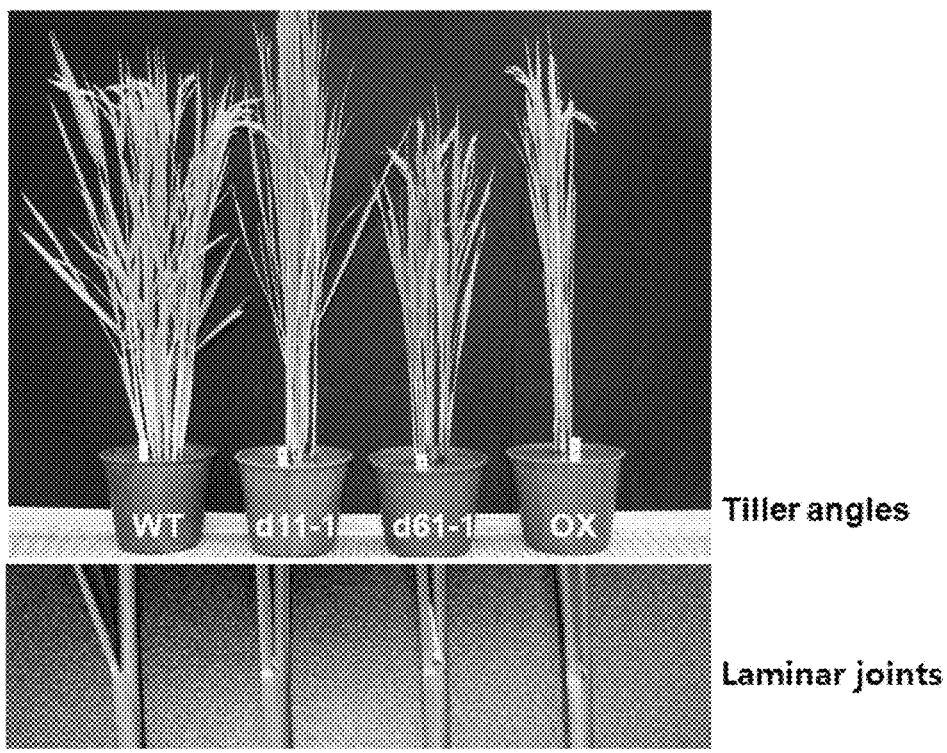
FIG. 5 illustrates BR mutants (d11-1 and d61-1) and OsMPT overexpressor (OX). Similar erect plant types are observed in BR mutants and OsMPT overexpressors. d11, that is also named CYP724B1 or DWARF4L, catalyzes the step of conversion of (6-deoxo) 3-dehydroteasterone) to (6-deoxo) typhasterol in the BR synthetic pathway. d61-1 is a weak allele of a rice bri1 orthologue, which is the BR-receptor kinase.
Figure 6:
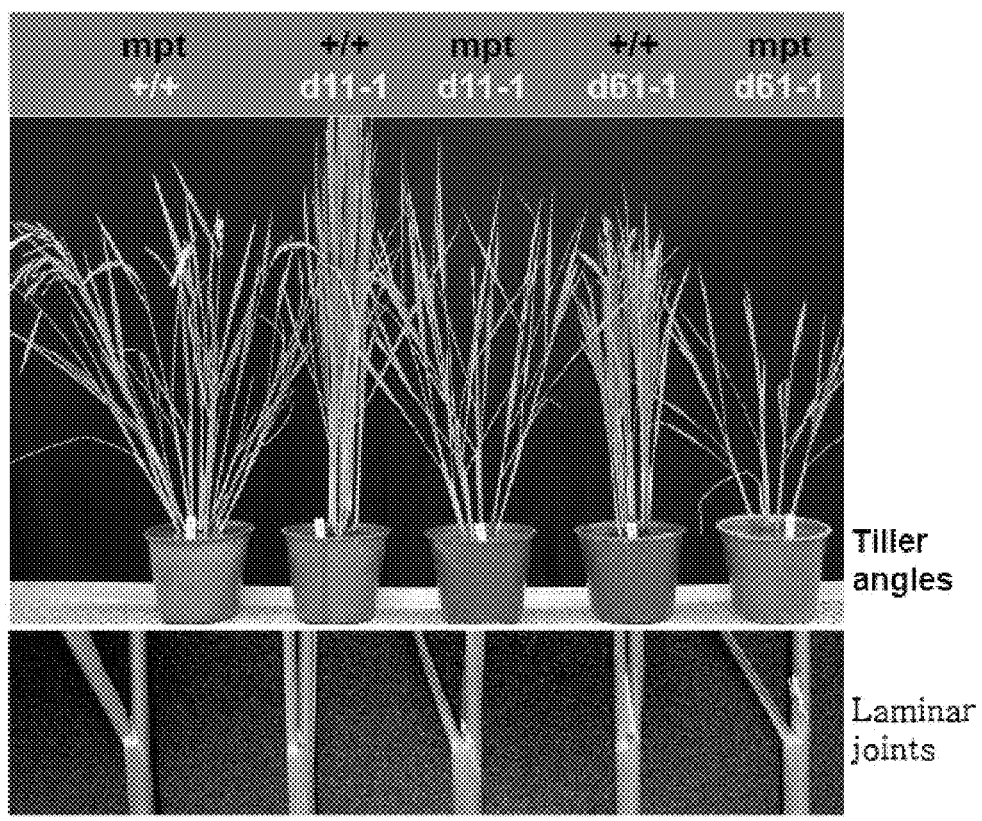
FIG. 6 illustrates comparison of phenotypes of double mutants between OsMPT and BR signal (d61-1) or synthetic (d11-1) mutant. Mature plants were isolated from cross-breeding between OsMPT and d61-1 or d11-1.
Figure 7:
FIG. 7 illustrates the erect plant type lines using OsMPT. Among OsMPT overexpressor (OX) lines, ones exhibiting high yield potentials in the densely planted field were selected. Dongjin rice cultivar is a Japonica rice variety and is a parental line of the OsMPT overexpressors.

OsMPT Mutants and Overexpressors Exert Opposite Effects on Tiller and Laminar Joint Angles OsMPT controls the angles of tillers and laminar joints (joints of blade and sheath). The mutants exhibit wider angles of tillers and laminar joints (FIG. 3). Whereas the OsMPT overexpressor develops narrow tiller angles and erect leaves (FIG. 4). Phenotypic expression of OsMPT overexpressors shows resemblance to those of BR (brassinosteroid) mutants (FIG. 5). Genetic analysis shows that OsMPT mutants are epistatic to BR signal mutant d61-1 and BR deficient mutant d11-1 in determining tiller angles (FIG. 6). OsMPT appears to work at the downstream of BR action.

Example 4

Agricultural Utility of OsMPT

Rice yield is greatly influenced by plant architectures that are defined by tiller number, tiller angle, internode elongation, panicle morphology, and leaf angle. Among them, tiller and leaf angles are the important factors since they can determine the efficiency of incident solar radiation on leaf surfaces. Until now, it is known that BR deficiency is an only known factor leading to erect plant type in rice. In this connection, by utilizing BR-deficient mutants, it has been demonstrated that erect type rice plants produce higher yield when they are densely planted (Sakamoto et al., 2006, *Nat. Biotechnol.* 24, 105-109). Since OsMPT takes action at the downstream of BR actions, a change in BR homeostasis is not expected in OsMPT transgenic plants. Also, OsMPT-overexpression strategy may be an easier approach than suppressing BR synthesis or signal genes.

Example 5

Analysis of Phenotype and Yield of OsMPT Overexpressor Lines in Paddy Field

Figure 8:
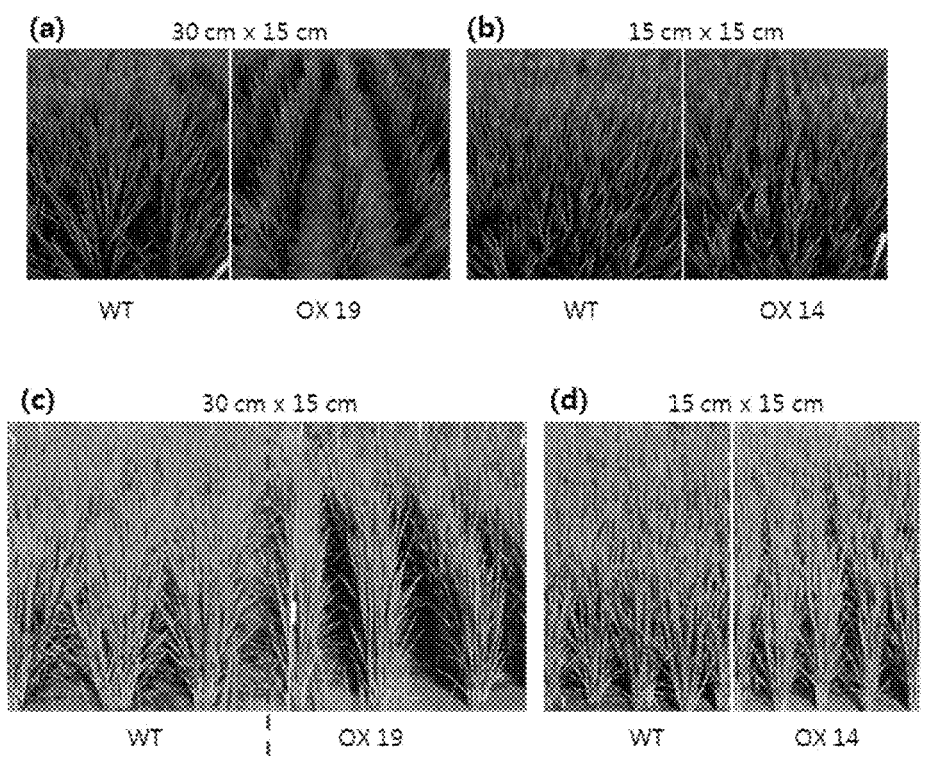
FIG. 8 illustrates OsMPT overexpressor line in a paddy field (around 2 month after transplantation). (a) and (c) show Dongjin rice cultivar (WT: non-transgenic control line) and the OsMPT overexpressor line (OX19) that are cultivated with standard transplantation distance of 30×15 cm. The vertical red dashed line in (c) indicates a boundary between the WT and OX19. (b) and (d) show Dongjin rice cultivar (WT) and the OsMPT overexpressor line (OX14) cultivated in high density (15×15 cm). (a) and (b) are the photographic images that are taken above the crops while (c) and (d) are the photographic images that are taken at almost the same height as the plants.
Figure 9:
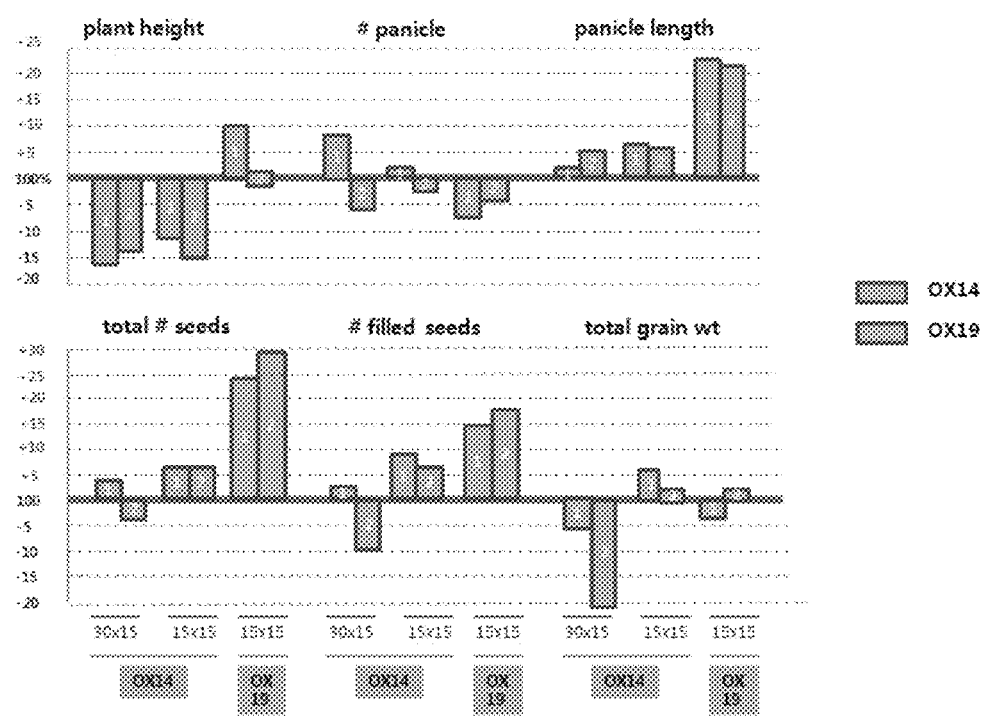
FIG. 9 illustrates the results of evaluating the phenotype and yield of a transgenic plant. All the data of overexpressor lines were divided by its non-transgenic control line (WT), and then converted to percentages that are also shown in the Table 1. The bars above the standard line (100%) indicate higher performance than the non-transgenic control line (i.e., WT). On the other hand, the bars below the standard line showed lower performance than the non-transgenic control line (i.e., WT).

In order to determine phenotype and yield of OsMPT overexpressor lines in a colony, the plants were cultivated in a GMO field at two different planting densities. As shown in FIG. 8, the OsMPT overexpressor lines showed strong erect growth both at standard cultivation distance (30×15 cm) and dense planting distance (15×15 cm). In particular, the OsMPT overexpressor lines showed a clean interval between rows as they had a well-defined space between the plants cultivated even at dense planting distance. In case of the dense planting, rice of a common type (i.e., Dongjin cultivar) showed lodging after rainy season. However, the OsMPT plant exhibited resistance to lodging so that it is found to have excellent adaptation for dense planting.

Results obtained from evaluating yield components of transgenic plants were expressed as average mean values ('AVE') and standard deviations ('S.D.'), as indicated in the Table 1. The mean values were the average of the number of plants shown in the fourth row of the Table 1.

TABLE 1

Harvest Index (Year 2010)

| | | OX14 | | | | | | OX19 | | | | |
|---|---|---|---|---|---|---|---|---|---|---|---|---|
| | | Standard Density | | | High Density | | | Standard Density | | | High Density | |
| | | WT | #1 | #2 | WT | #1 | #2 | WT | #1 | #2 | WT | #1 | #2 |
| | | 29 | 28 | 27 | 60 | 60 | 60 | 23 | 27 | 60 | 51 | 60 |
| PH (cm) | AVE | 113.9 | 96.18 | 97.72 | 114.9 | 101.7 | 97.5 | 120.4 | 120.2 | 115.3 | 127.1 | 115.4 |
| | % | 100%* | 84.4% | 85.8% | 100% | 88.5% | 84.9% | | | 100% | 110.2% | 100% |
| | S.D. | 7.04 | 1.98 | 1.39 | 4.21 | 4.31 | 2.89 | 3.81 | 4.79 | 2.86 | 3.00 | 2.83 |
| PN | AVE | 11.83 | 12.77 | 11.13 | 6.92 | 7.04 | 6.88 | 8.43 | 9.63 | 7.22 | 6.67 | 6.90 |
| | % | 100% | 108.0% | 94.0% | 100% | 101.7% | 97.5% | | | 100% | 92.4% | 95.6% |
| | S.D. | 2.054 | 2.43 | 2.61 | 1.52 | 1.31 | 1.34 | 1.47 | 1.80 | 1.29 | 1.59 | 1.68 |
| PL (cm) | AVE | 22.1 | 22.5 | 23.3 | 21.2 | 22.5 | 22.4 | 28.3 | 26.9 | 21.6 | 26.3 | 26.1 |
| | % | 100% | 101.8% | 105.4% | 100% | 106.1% | 105.6% | | | 100% | 121.8% | 120.8% |
| | S.D. | 1.37 | 1.17 | 1.10 | 1.096 | 1.09 | 1.15 | 1.29 | 1.2 | 1.56 | 1.6 | 1.5 |
| TNS | AVE | 1278.66 | 1328.57 | 1227.78 | 632.77 | 675.18 | 673.20 | 1103.78 | 1203.89 | 660.05 | 822.71 | 854.28 |
| | % | 100% | 103.9% | 96.0% | 100% | 106.7% | 106.4% | | | 100% | 124.6% | 129.4% |
| | S.D. | 235.99 | 251.21 | 272.04 | 155.99 | 162.08 | 122.01 | 214.48 | 218.10 | 140.60 | 207.24 | 212.18 |
| NFG | AVE | 1058.24 | 1084.93 | 955.19 | 507.38 | 547.68 | 526.64 | 912.13 | 973.81 | 585.43 | 671.27 | 692.12 |
| | % | 100% | 102.5% | 90.3% | 100% | 107.9% | 106.4% | | | 100% | 114.7% | 118.2% |
| | S.D. | 196.50 | 247.52 | 181.58 | 130.88 | 143.28 | 99.12 | 189.28 | 172.32 | 131.12 | 188.26 | 177.56 |

TABLE 1-continued

Harvest Index (Year 2010)

| | | Line | | | | | | | | | | |
|---|---|---|---|---|---|---|---|---|---|---|---|---|
| | | OX14 | | | | | | OX19 | | | | |
| | | Density | | | | | | | | | | |
| | | Standard Density | | | High Density | | | Standard Density | | | High Density | |
| | | | | | Lines | | | | | | | |
| | | WT | #1 | #2 | WT | #1 | #2 | WT | #1 | #2 | WT | #1 | #2 |
| | | | | | | | Total plants | | | | | |
| | | 29 | 28 | 27 | 60 | 60 | 60 | 23 | 27 | 60 | 51 | 60 |
| TGW | AVE | 25.51 | 24.04 | 20.78 | 11.97 | 12.63 | 12.42 | | 17.70 | 17.94 | 13.79 | 13.33 | 13.91 |
| (gm) | % | 100% | 94.0% | 81.5% | 100% | 105.5% | 103.8% | | | | 100% | 96.7% | 100.8% |
| | S.D. | 5.45 | 6.34 | 4.46 | 3.67 | 3.58 | 2.51 | | 4.40 | 3.00 | 3.56 | 3.93 | 4.30 |

PH, plant height;
PN, panicle number;
PL, panicle length;
TNS; total number of seeds;
NFG, total number of fertile grain;
TGW, total grain weight
AVE, average;
S.D., standard deviation;
%, ratios of MPT1 to its wild type sibling Among the OsMPT lines, the panicle length was about 5 to 20% higher in OX19 lines compared to WT (non-transgenic line). Compared to the non-transgenic control line, the OsMPT lines had increased total number of seeds in high density field than in standard density field. Total seed number was higher in OsMPT OX lines than the non-transgenic control line, i.e., about 6 to 30% higher than the control. OsMPT plants in high density field showed higher filled seed ratio compared to ones in the standard density field. OsMPT produced much higher number of filled seeds than the to non-transgenic control line, i.e., 6 to 20% higher than the control. Total grain weight per plant was also increased up to 5% in the OsMPT line.

OsMPT OX lines showed better performance in the high density planting. Further, OsMPT OX exhibited increased panicle length, total grain number, filled seeds, and total grain weight per plant.

What is claimed is:

1. A method for modifying a tiller angle or a laminar joint angle, the method comprising:
transforming a plant with a gene encoding a polypeptide having the amino acid sequence of SEQ ID NO: 1 to increase or decrease expression of the polynucleotide within a cell, as compared to wild type expression.

2. The method according to claim 1, wherein the polynucleotide has the base sequence represented by SEQ ID NO: 2.

3. The method according to claim 1, wherein the plant is selected from angiosperms including rice, wheat, barley, oat, rye, lawn grass, bamboo shoot, corn, sugar cane, millet, taro, asparagus, onion, garlic, scallion, leek, wild rocambole, hemp, ginger, bean, and canola.

4. The method according to claim 1, wherein the cell is a cell of plant pulvinus tissue.

5. A method for producing a plant, the method comprising transforming a plant with a gene encoding a polypeptide having the amino acid sequence of SEQ ID NO:1 to modify a tiller angle or a laminar joint angle.

6. The plant produced by the method of claim 5.

7. The method according to claim 5, wherein the plant is selected from angiosperms including rice, wheat, barley, oat, rye, lawn grass, bamboo shoot, corn, sugar cane, millet, taro, asparagus, onion, garlic, scallion, leek, wild rocambole, hemp, ginger, bean, and canola.

8. The method according to claim 1, wherein the plant is rice.

9. The method according to claim 5, wherein the plant is rice.

* * * * *

```
                        SEQUENCE LISTING

<160> NUMBER OF SEQ ID NOS: 12

<210> SEQ ID NO 1
<211> LENGTH: 438
<212> TYPE: PRT
<213> ORGANISM: Oryza sativa

<400> SEQUENCE: 1

Met Ala Leu Val Lys Ser His His Gln Met Leu Ala Ser Ser Ser Thr
1               5                   10                  15

Ser Ser Ser Ser Pro Ser Ser Gln Gln Gln Gln Pro Pro Pro Pro Ala
            20                  25                  30

Ser Asn Ser Ser Ser Leu Ala Ala Ala Ala Ala Asp Gln Pro Ser Pro
        35                  40                  45

Ala Lys Arg Lys Arg Pro Pro Gly Thr Pro Asp Pro Asp Ala Glu
    50                  55                  60

Val Val Ala Leu Ser Pro Arg Thr Leu Leu Glu Ser Asp Arg Tyr Val
65                  70                  75                  80

Cys Glu Ile Cys Gly Gln Gly Phe Gln Arg Glu Gln Asn Leu Gln Met
                85                  90                  95

His Arg Arg Arg His Lys Val Pro Trp Arg Leu Val Lys Arg Pro Ala
            100                 105                 110

Ala Ala Thr Ala Ala Glu Asp Gly Gly Ala Ala Gly Gly Gly Gly
        115                 120                 125

Ala Gly Gly Gly Ala Gly Gly Gly Gly Ala Arg Lys Arg Val Phe Val
```

```
Cys Pro Glu Pro Ser Cys Leu His His Asp Pro Ala His Ala Leu Gly
145                 150                 155                 160

Asp Leu Val Gly Ile Lys Lys His Phe Arg Arg Lys His Gly Gly Arg
                165                 170                 175

Arg Gln Trp Val Cys Ala Arg Cys Ala Lys Gly Tyr Ala Val Gln Ser
            180                 185                 190

Asp Tyr Lys Ala His Leu Lys Thr Cys Gly Thr Arg Gly His Ser Cys
        195                 200                 205

Asp Cys Gly Arg Val Phe Ser Arg Val Glu Ser Phe Ile Glu His Gln
    210                 215                 220

Asp Ala Cys Asn Ser Gly Arg Val Arg Gly Glu Val Val Pro Val Ala
225                 230                 235                 240

Thr Thr Leu Pro Val Ile Arg Pro Ala Ala Leu Arg His His His His
                245                 250                 255

His Pro Pro Pro Pro Pro Glu Leu Gln Leu Leu Pro Ala Ser Thr
            260                 265                 270

Thr Ala Pro Leu Ala Ala Ala Phe Ser Ser Asn Ser Thr Thr Thr Gly
        275                 280                 285

Ser Ser Ser His Glu Gln His Ala Thr Thr Met Thr Thr Thr Lys Leu
    290                 295                 300

Gln Leu Ser Ile Gly Pro Ala Ala Val Val Ala Ala Ala Ser Gly Gly
305                 310                 315                 320

Gly Gly Ala Cys Ala Ala Ala Gly Gly Glu Glu Glu Gln Gln Arg
                325                 330                 335

Glu Glu Val Arg Arg Ala Leu Glu Glu Lys Thr Ala Ala Asp Ala Ala
            340                 345                 350

Arg Glu Arg Ala Arg Glu Glu Ala Ala Ala Glu Arg Ala Leu Glu
        355                 360                 365

Asp Ala Arg Arg Ala Arg His Arg Ala Arg Gly Glu Leu Glu Lys Ala
    370                 375                 380

Leu Ala Leu Arg Asp His Ala Ala Arg Leu Ile Ala Gln Val Thr Cys
385                 390                 395                 400

His Ala Cys Arg Gln Arg Ser Leu Ala Val Met Ser Met Ala Ile
                405                 410                 415

Asp Gly His Gly Ala Ser Ala Val Ala Arg Glu His Leu Arg Gly Gly
            420                 425                 430

Gly Val Gly Ala Gly Ile
        435
```

<210> SEQ ID NO 2
<211> LENGTH: 1317
<212> TYPE: DNA
<213> ORGANISM: Oryza sativa

<400> SEQUENCE: 2

```
atggcactgg tcaagagcca ccaccaaatg ttggcctctt cttccacctc gtcctcctca      60
ccctcctccc agcagcagca gcctccaccg ccggcgtcga actcctccag cctcgccgcc     120
gccgccgccg accagccctc ccccgccaag cgcaagaggc ccctcccggc acgccagac     180 ccagatgcgg aggtggtggc gctgtcgccg aggacgctgc tggagtcgga caggtacgtg     240
tgcgagatct gcgggcaggg gttccagcgg gagcagaacc tgcagatgca ccggcgccgg     300
cacaaggtgc cgtggcggct ggtcaagcgc ccgcggcgg cgacggcggc ggaggacggc     360
```

-continued

```
ggcgccgcgg gtggcggcgg cggcgccggc ggcggcgcgg gcggcggagg ggcgcggaag        420
cgcgtgttcg tgtgcccgga gccgagctgc ctccaccacg acccggcaca cgcgctgggc        480
gacctcgtcg gcatcaagaa gcacttccgg cgcaagcacg gcggccggcg gcagtgggtg        540
tgtgcccgct gcgccaaggg ctacgccgtc cagtccgact acaaggccca cctcaagacc        600
tgcggcaccc gcggccactc ctgcgactgc ggccgcgtct tctcccgagt ggagagcttc        660
atagagcacc aggatgcgtg taactctgga cgtgtgcgcg gtgaggtcgt gcccgtggcc        720
acgacgctgc cggtcatccg tcccgcggcg ctgcggcatc atcaccatca tccgccgccg        780
ccgccgcctg agctgcagct cctcccggcg tccaccacgg cgccgttggc cgccgcgttc        840
tcgtccaact ccacgaccac cggctcctcc tcccacgagc aacacgcgac gacgatgaca        900
acgacgaagc tgcagctctc aatcggcccc gccgccgtcg tcgccgcggc gtccggcggc        960
ggcggcgcct gcgccgcggc ggcaggaggg gaggaggagc agcagcggga agaggtgagg       1020
cgcgcgctgg aggagaagac cgcggcggac gcggcgcggg agcgggcgcg cgaggaggcc       1080 gcggcggcg agcgcgcgct ggaggacgcc cgccgcgcgc gccaccgggc gcgcggggag       1140
ctcgagaagg cgctcgcgct gcgggaccac gcggcgcgcc tgatcgcgca ggtgacctgc       1200
cacgcgtgcc ggcagcgctc gctcgccgtg atgtccatgg ccgccatcga cggccacggc       1260
gcgtcggcgg tggcgcgcga gcacctgagg ggcggcggcg tcggcgccgg catctag         1317
```

<210> SEQ ID NO 3
<211> LENGTH: 4284
<212> TYPE: DNA
<213> ORGANISM: Oryza sativa

<400> SEQUENCE: 3

```
acacaaacac atacacacac aatgcacctt cacctttcca ccccataaag cctcccttgg         60
cacccctatc ccactaagga gcaaaaagag aaccaaacca aggcagctgc tgcagaggca        120
gtagtagtag tagtagaagt agctgctgtg atctagcctc ttgtggtggt agctctagct        180
ctagaagtgg tattgtggtg ataagcttaa gcttaagctt attagtgatc ctctccctta        240
aaaagaagaa aagctccttg cagttatggc actggtcaag agccaccacc aaatgttggc        300
ctcttcttcc acctcgtcct cctcacccta ctcccagcag cagcagcctc caccgccggc        360
gtcgaactcc tccagcctcg ccgccgccgc cgccgaccag ccctcccccg ccaagcgcaa        420
gaggcgccct cccggcacgc caggtacgta tatacgtatg tgttggagac attgatacca        480
tcatgcatgc atggtgttcg atcatggagc ccgtgtgtac gtagacccag atgcggaggt        540
ggtggcgctg tcgccgagga cgctgctgga gtcggacagg tacgtgtgcg agatctgcgg        600
gcaggggttc cagcgggagc agaacctgca gatgcaccgg cgccggcaca aggtgccgtg        660
gcggctggtc aagcgccccg cggcggcgac ggcggcggag gacggcggcg ccgcgggtgg        720
cggcggcggc gccggcggcg gcgcgggcgg cggaggggcg cggaagcgcg tgttcgtgtg        780
cccggagccg agctgcctcc accacgaccc ggcacacgcg ctgggcgacc tcgtcggcat        840
caagaagcac ttccggcgca agcacggcgg ccggcggcag tgggtgtgtg cccgctgcgc        900
caagggctac gccgtccagt ccgactacaa ggcccacctc aagacctgcg gcacccgcgg        960
ccactcctgc gactgcggcc gcgtcttctc ccggtacgta caccaccccc tctcctcctc       1020
ctcaaaccta cgtagcgttc atggcggccg gcgacgcatg cactactact actacgtacg       1080
aacgctaacc atccatgatt agcgattgat acgatgacgt ttgggtggtt ggatatatat       1140
catgattatg tgcatacgta attagatctt ggagtattta gatttaaaga gatgaatttc       1200
```

```
gaattgtttt tggtgggaga cagggttgca tggagataag acaaaagcta tggtacgttt   1260
cagggtttaa aacctgccac tgggctgtag atatgatatc gccactcgga gagagaaaaa   1320
agaaaaaaag aaaattaaaa ggatgtgtgt ttttgtagcc gacaccaatt gactagctat   1380
agtttgatct gatcgatccg ttgtttaact ggctagctag ctgaccaaag aaagagcata   1440
tttatgtacg gactaattgg atcgggacta ttactactac ttcaggttct tgctgttgat   1500
gcatgctgat cacttacata catacatcct gctaggtagc tagggtccag tagtacgcat   1560
atatccatcg agattaatcg aaaactattt tctagctaga ctgaaaaagg gagagaaaaa   1620
attaaatcag aggagatcga tgagatcatg aagagatga aaaagcaggg cagacgcctg    1680
gcatatgatc gtttcggtgg cgggttgcgg taggaccgaa aattcctaca ggaaagcgac   1740
cgcatatcga ccaaaaactg tctctgcgca tttcacccaa cagctaagct aagtgtagta   1800
gtagcagcga tagctccagc ttccggccag ttacgctgat aagatggctg gttgttgtag   1860
tcctaactca aagtaagtaa aacatgagcg ccactgtttg ttcatgtgca aacataatgc   1920
ctgccagagc taatcagcca ttaatagctt gtaggagtag cattttagca tgcgagttac   1980
tagcagctat ttatggatct taattctgtg aaaacttatc aggtggctgt agtaactgct   2040
atcgtcacgt aactttaacc acaaattact tttaaataat tacttcctcc aatccatatt   2100
atcagttgtt ttgtcaaagt caaacttctt caaatctaac caagtttata ggaaaaagta   2160
gtaacatttt caacccaaaa caaatttgtt acgaaaatat attcaattat tgatttgatg   2220
aaactaattt ggtgttgtaa atattactat atttatctat aaacttagtc aaatttaaag   2280
cagtttgatt ttgatcaaag tcaaaacgat ttataacctg aaacggaggg agaacattat   2340
aattaagaaa acttgtgtgg ttatattaat gatgatgtac acttcggtaa tataacatat   2400
ttttaagtag tatttatttt tttccagaaa aattaccaga agtttaaacc tgtatagtga   2460
catagccaat tatttaagaa tgaagtatat aatatctcta tcaaatatag caatcaagta   2520
cgtgatagga taatcctgac ctgcctagat ttacagtaat agaattagaa tgtgtgtttg   2580
atcccgtaat agaacggaca ctagtactac atgtagatgt cctagggagt gagatgatgt   2640
ggacgaggca aggtgcaagg tgacgaagca gaggtcgcta ggtaggtaaa gacaagctgc   2700
tccattcctc ggaccctgg atccaccacc aaagtacaac cacgcgcgga cggggcacat   2760
caccagatcg cccggagcta agctatacac aggccaccat gtgcacccat ccatcatcca   2820
tgcacacaca acagcatcat ctcctcctct gttttttct ctccaggaca agagcttccc    2880
actaggcgat cgctttaata attggcagta gctaagccac actctcttgt cactgaccag   2940
cccataaata taccggacga gcagcagcat cagcagcata tgcagcatgt tttcccctgc   3000
agataccgat atgatcgttg cttcttccat atgtcgtcgt cgtcgtcgac gactggtttt   3060
ctagctcgat caataatggc gtaagtgcag gcgccatcac tagctagctg tgtgtgtagt   3120
atatgtgtac agtgctgctg ttggttggtc ccttggacgg actggtcgcg cgtggccatt   3180
tagtcagcaa tggaacgtag ctagcttcct tgatgggttt aacgatggca tatggtggtc   3240
catcccatgg gtttcatctg gttgtctcat gctctcatcg atctgtcagt gtgtgtcttg   3300
ttcgagatcg atgcgttgct ttcgatcgat ctacatgtac agatgatcaa tcagtcgatc   3360
agatcgatcg ccgtgttttt gttgtgtttg gtgataagat ggtggttaag tggtatgatt   3420
agtgtgtgct aatggcggtg gttgtgtgtg ttggttgcag agtggagagc ttcatagagc   3480
accaggatgc gtgtaactct ggacgtgtgc gcggtgaggt cgtgcccgtg gccacgacgc   3540
```

```
tgccggtcat ccgtcccgcg gcgctgcggc atcatcacca tcatccgccg ccgccgccgc    3600
ctgagctgca gctcctcccg gcgtccacca cggcgccgtt ggccgccgcg ttctcgtcca    3660
actccacgac caccggctcc tcctcccacg agcaacacgc gacgacgatg acaacgacga    3720
agctgcagct ctcaatcggc cccgccgccg tcgtcgccgc ggcgtccggc ggcggcggcg    3780
cctgcgccgc ggcggcagga ggggaggagg agcagcagcg ggaagaggtg aggcgcgcgc    3840
tggaggagaa gaccgcggcg gacgcggcgc gggagcgggc gcgcgaggag gccgcggcgg    3900
cggagcgcgc gctggaggac gcccgccgcg cgcgccaccg ggcgcgcggg gagctcgaga    3960
aggcgctcgc gctgcgggac cacgcggcgc gcctgatcgc gcaggtgacc tgccacgcgt    4020
gccggcagcg ctcgctcgcc gtgatgtcca tggccgccat cgacggccac ggcgcgtcgg    4080
cggtggcgcg cgagcacctg aggggcggcg gcgtcggcgc cggcatctag ctgatatgta    4140
catgcatgca catgtacaac ttgtacgttc acgtgtgtac gtgcacgcgt atgtatgtaa    4200 agcaagggg gttgggtgac gacggtgtaa ttcatctttt tttttagccg caaattgatg    4260
aagtgtacgt agtttcgtag gtcg                                          4284
```

<210> SEQ ID NO 4  
<211> LENGTH: 27  
<212> TYPE: DNA  
<213> ORGANISM: Artificial Sequence  
<220> FEATURE:  
<223> OTHER INFORMATION: OsMPT 5 Race-PCR primer

<400> SEQUENCE: 4
acctgtccga ctccagcagc gtcctcg                                         27

<210> SEQ ID NO 5  
<211> LENGTH: 26  
<212> TYPE: DNA  
<213> ORGANISM: Artificial Sequence  
<220> FEATURE:  
<223> OTHER INFORMATION: OsMPT 3 Race-PCR primer

<400> SEQUENCE: 5
gtacaacttg tacgttcacg tgtgta                                          26

<210> SEQ ID NO 6  
<211> LENGTH: 19  
<212> TYPE: DNA  
<213> ORGANISM: Artificial Sequence  
<220> FEATURE:  
<223> OTHER INFORMATION: OsMPT RT-PCR primer-a

<400> SEQUENCE: 6
cggcatcaag aagcacttc                                                  19

<210> SEQ ID NO 7  
<211> LENGTH: 22  
<212> TYPE: DNA  
<213> ORGANISM: Artificial Sequence  
<220> FEATURE:  
<223> OTHER INFORMATION: OsMPT RT-PCR primer-b

<400> SEQUENCE: 7
ggatgatggt gatgatgccg ca                                              22

<210> SEQ ID NO 8  
<211> LENGTH: 18  
<212> TYPE: DNA  
<213> ORGANISM: Artificial Sequence

```
<220> FEATURE:
<223> OTHER INFORMATION: ACT1 primer-a

<400> SEQUENCE: 8
cgaggcgcag tccaagag                                                        18

<210> SEQ ID NO 9
<211> LENGTH: 20
<212> TYPE: DNA
<213> ORGANISM: Artificial Sequence
<220> FEATURE:
<223> OTHER INFORMATION: ACT1 primer-b

<400> SEQUENCE: 9
cccagttgct gacgatacca                                                      20

<210> SEQ ID NO 10
<211> LENGTH: 19
<212> TYPE: DNA
<213> ORGANISM: Artificial Sequence
<220> FEATURE:
<223> OTHER INFORMATION: OsMPT primer-a

<400> SEQUENCE: 10
cggcatcaag aagcacttc                                                       19

<210> SEQ ID NO 11
<211> LENGTH: 22
<212> TYPE: DNA
<213> ORGANISM: Artificial Sequence
<220> FEATURE:
<223> OTHER INFORMATION: OsMPT primer-b

<400> SEQUENCE: 11
ggatgatggt gatgatgccg ca                                                   22

<210> SEQ ID NO 12
<211> LENGTH: 439
<212> TYPE: PRT
<213> ORGANISM: Arabidopsis thaliana

<400> SEQUENCE: 12
```

Met Leu Ser Asn Lys Asn Thr Asn Thr Cys Cys Val Val Ser Ser Ser
1               5                   10                  15

Ser Ser Asp Pro Phe Leu Ser Ser Glu Asn Gly Val Thr Thr Thr
            20                  25                  30

Asn Thr Ser Thr Gln Lys Arg Lys Arg Arg Pro Ala Gly Thr Pro Asp
        35                  40                  45

Pro Asp Ala Glu Val Val Ser Leu Ser Pro Arg Thr Leu Leu Glu Ser
    50                  55                  60

Asp Arg Tyr Ile Cys Glu Ile Cys Asn Gln Gly Phe Gln Arg Asp Gln
65                  70                  75                  80

Asn Leu Gln Met His Arg Arg Arg His Lys Val Pro Trp Lys Leu Leu
                85                  90                  95

Lys Arg Asp Asn Asn Ile Glu Val Lys Lys Arg Val Tyr Val Cys Pro
            100                 105                 110

Glu Pro Thr Cys Leu His His Asn Pro Cys His Ala Leu Gly Asp Leu
        115                 120                 125

Val Gly Ile Lys Lys His Phe Arg Arg Lys His Ser Asn His Lys Gln
    130                 135                 140

Trp Val Cys Glu Arg Cys Ser Lys Gly Tyr Ala Val Gln Ser Asp Tyr

```
145                 150                 155                 160
Lys Ala His Leu Lys Thr Cys Gly Thr Arg Gly His Ser Cys Asp Cys
                165                 170                 175

Gly Arg Val Phe Ser Arg Val Glu Ser Phe Ile Glu His Gln Asp Asn
                180                 185                 190

Cys Ser Ala Arg Arg Val His Arg Glu Pro Pro Arg Pro Pro Gln Thr
            195                 200                 205

Ala Val Thr Val Pro Ala Cys Ser Ser Arg Thr Ala Ser Thr Val Ser
        210                 215                 220

Thr Pro Ser Ser Glu Thr Asn Tyr Gly Gly Thr Val Ala Val Thr Thr
225                 230                 235                 240

Pro Gln Pro Leu Glu Gly Arg Pro Ile His Gln Arg Ile Ser Ser Ser
                245                 250                 255

Ile Leu Thr Asn Ser Ser Asn Asn Leu Asn Leu Glu Leu Gln Leu Leu
                260                 265                 270

Pro Leu Ser Ser Asn Gln Asn Pro Asn Gln Glu Asn Gln Gln Gln Lys
            275                 280                 285

Val Lys Glu Pro Ser His His His Asn His Asn His Asp Thr Thr Asn
    290                 295                 300

Leu Asn Leu Ser Ile Ala Pro Ser Ser Ser Tyr Gln His Tyr Asn Asn
305                 310                 315                 320

Phe Asp Arg Ile Lys Glu Ile Met Ala Ser Glu Gln Ile Met Lys Ile
                325                 330                 335

Ala Met Lys Glu Lys Ala Tyr Ala Glu Glu Ala Lys Arg Glu Ala Lys
            340                 345                 350

Arg Gln Arg Glu Ile Ala Glu Asn Glu Phe Ala Asn Ala Lys Lys Ile
        355                 360                 365

Arg Gln Lys Ala Gln Ala Glu Leu Glu Arg Ala Lys Phe Leu Lys Glu
    370                 375                 380

Gln Ser Met Lys Lys Ile Ser Ser Thr Ile Met Gln Val Thr Cys Gln
385                 390                 395                 400

Thr Cys Lys Gly Gln Phe Gln Ala Val Ala Val Pro Ala Ala Thr Ala
                405                 410                 415

Asp Glu Thr Ser Leu Val Val Ser Tyr Met Ser Ser Ala Asn Thr Asp
            420                 425                 430

Gly Glu Leu Glu Asn Gly Phe
            435
```